(12) United States Patent
Howard

(10) Patent No.: US 11,596,526 B2
(45) Date of Patent: Mar. 7, 2023

(54) SYSTEMS AND METHODS FOR EXPANDABLE CORPECTOMY SPACER IMPLANTATION

(71) Applicant: GLOBUS MEDICAL, INC., Audubon, PA (US)

(72) Inventor: George Howard, Green Lane, PA (US)

(73) Assignee: Globus Medical Inc., Audubon, PA (US)

(*) Notice: Subject to any disclaimer, the term of this patent is extended or adjusted under 35 U.S.C. 154(b) by 190 days.

(21) Appl. No.: 17/094,177

(22) Filed: Nov. 10, 2020

(65) Prior Publication Data
US 2021/0059835 A1   Mar. 4, 2021

Related U.S. Application Data

(63) Continuation-in-part of application No. 16/371,419, filed on Apr. 1, 2019, now Pat. No. 10,881,528, which is a continuation of application No. 15/836,362, filed on Dec. 8, 2017, now Pat. No. 10,278,834, which is a continuation-in-part of application No. 15/264,974, filed on Sep. 14, 2016, now Pat. No. 10,278,833.

(51) Int. Cl.
A61F 2/44 (2006.01)

(52) U.S. Cl.
CPC .............. A61F 2/4465 (2013.01); A61F 2/44 (2013.01); A61F 2/446 (2013.01); A61F 2002/448 (2013.01); A61F 2002/4495 (2013.01)

(58) Field of Classification Search
CPC .......... A61F 2/44; A61F 2/442; A61F 2/4455; A61F 2/4465; A61F 2002/443; A61F 2002/4435
See application file for complete search history.

(56) References Cited

U.S. PATENT DOCUMENTS

| 5,192,327 | A |   | 3/1993  | Brantigan        |            |
|-----------|---|---|---------|------------------|------------|
| 5,571,190 | A |   | 11/1996 | Ulrich et al.    |            |
| 5,702,451 | A |   | 12/1997 | Biedermann et al.|            |
| 5,702,455 | A | * | 12/1997 | Saggar           | A61F 2/44  |
|           |   |   |         |                  | 623/17.15  |
| 5,897,556 | A |   | 4/1999  | Drewry et al.    |            |
| 6,086,613 | A |   | 7/2000  | Camino           |            |
| 6,159,211 | A |   | 12/2000 | Boriani et al.   |            |
| 6,758,862 | B2|   | 7/2004  | Berry et al.     |            |
| 6,776,798 | B2|   | 8/2004  | Camino et al.    |            |

(Continued)

FOREIGN PATENT DOCUMENTS

| AU | 2008224951 A1 * | 9/2009 | ............... A61F 2/44 |
| CN | 1483389 A       | 3/2004 |                           |

(Continued)

Primary Examiner — Eric S Gibson

(57) ABSTRACT

An implant assembly including an expandable vertebral body replacement implant. Two outer cores disposed on opposing ends of an inner are configured to move away from each other when the inner core is actuated. The implant assembly may include removable endplate configured to engage vertebral bodies as interbody spacer or through a corpectomy. The implant may include a locking mechanism to prevent collapse or movement the implant assembly after implantation. The locking mechanism may be automatically engage after removal of an inserter instrument from the implant assembly.

18 Claims, 21 Drawing Sheets

(56) References Cited

U.S. PATENT DOCUMENTS

| | | | |
|---|---|---|---|
| 6,899,734 B2 | 5/2005 | Castro et al. | |
| 7,309,358 B2 | 12/2007 | Berry et al. | |
| 7,473,277 B2* | 1/2009 | Boyer, II | A61F 2/4465 623/17.11 |
| 7,575,601 B2* | 8/2009 | Dickson | A61F 2/44 623/17.15 |
| 7,887,594 B2 | 2/2011 | Berry et al. | |
| 8,182,537 B2* | 5/2012 | Refai | A61F 2/44 623/17.16 |
| 8,197,546 B2* | 6/2012 | Doubler | A61F 2/44 606/279 |
| 8,231,681 B2* | 7/2012 | Castleman | A61F 2/44 623/17.16 |
| 8,273,126 B2* | 9/2012 | Lindner | A61F 2/4611 623/17.11 |
| 8,282,683 B2* | 10/2012 | McLaughlin | A61F 2/4455 623/17.11 |
| 8,292,963 B2* | 10/2012 | Miller | A61F 2/44 606/252 |
| 8,900,308 B2* | 12/2014 | Biedermann | A61F 2/4465 623/17.11 |
| 9,301,850 B2* | 4/2016 | McLaughlin | A61F 2/446 |
| 9,474,621 B2* | 10/2016 | McLaughlin | A61F 2/4455 |
| 9,687,357 B2* | 6/2017 | Bannigan | A61F 2/4455 |
| 10,758,365 B2* | 9/2020 | Cummins | A61F 2/30771 |
| 2003/0191531 A1 | 10/2003 | Berry et al. | |
| 2004/0049270 A1 | 3/2004 | Gewirtz | |
| 2005/0090898 A1* | 4/2005 | Berry | A61F 2/44 623/17.11 |
| 2007/0255421 A1* | 11/2007 | Dickson | A61F 2/44 623/17.15 |
| 2009/0036985 A1 | 2/2009 | Whiting | |
| 2009/0112325 A1* | 4/2009 | Refai | A61F 2/44 623/17.15 |
| 2009/0187248 A1 | 7/2009 | Dewey et al. | |
| 2010/0274357 A1* | 10/2010 | Miller | A61F 2/4611 623/17.11 |
| 2011/0106258 A1 | 5/2011 | Blackwell et al. | |
| 2011/0251691 A1* | 10/2011 | McLaughlin | A61F 2/44 623/17.16 |
| 2012/0265303 A1* | 10/2012 | Refai | A61F 2/4465 623/17.11 |
| 2013/0331943 A1* | 12/2013 | Arnold | A61F 2/28 623/17.15 |
| 2014/0142706 A1* | 5/2014 | Hansell | A61F 2/442 623/17.16 |
| 2014/0156006 A1* | 6/2014 | Bannigan | A61F 2/44 623/17.15 |
| 2014/0207235 A1 | 7/2014 | Drapeau | |
| 2016/0100955 A1* | 4/2016 | Stinchfield | A61F 2/4465 623/17.15 |
| 2018/0318107 A1* | 11/2018 | Cummins | A61F 2/30771 |
| 2021/0059835 A1* | 3/2021 | Howard | A61F 2/30744 |
| 2021/0330471 A1* | 10/2021 | Dewey | A61F 2/446 |
| 2022/0023066 A1* | 1/2022 | Howard | A61F 2/4611 |
| 2022/0241085 A1* | 8/2022 | Berry | A61F 2/4425 |

FOREIGN PATENT DOCUMENTS

| | | | | |
|---|---|---|---|---|
| EP | 2421477 B1 * | 2/2014 | | A61F 2/44 |
| JP | 2001526083 | 12/2001 | | |
| JP | 2001526083 A | 12/2001 | | |
| JP | 2011502004 A | 1/2011 | | |
| WO | 9932055 A1 | 7/1999 | | |
| WO | 01/70139 A2 | 9/2001 | | |
| WO | 0170139 A2 | 9/2001 | | |
| WO | 2005070346 A1 | 8/2005 | | |
| WO | WO-2010124008 A2 * | 10/2010 | | A61F 2/44 |

\* cited by examiner

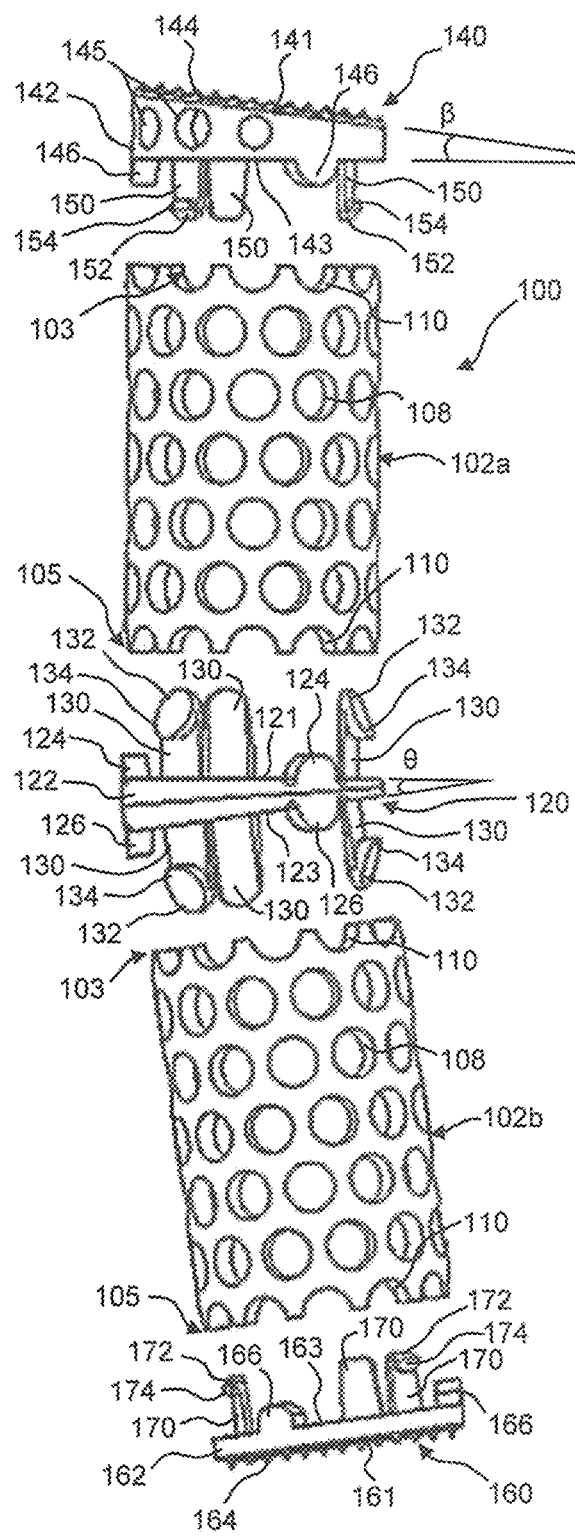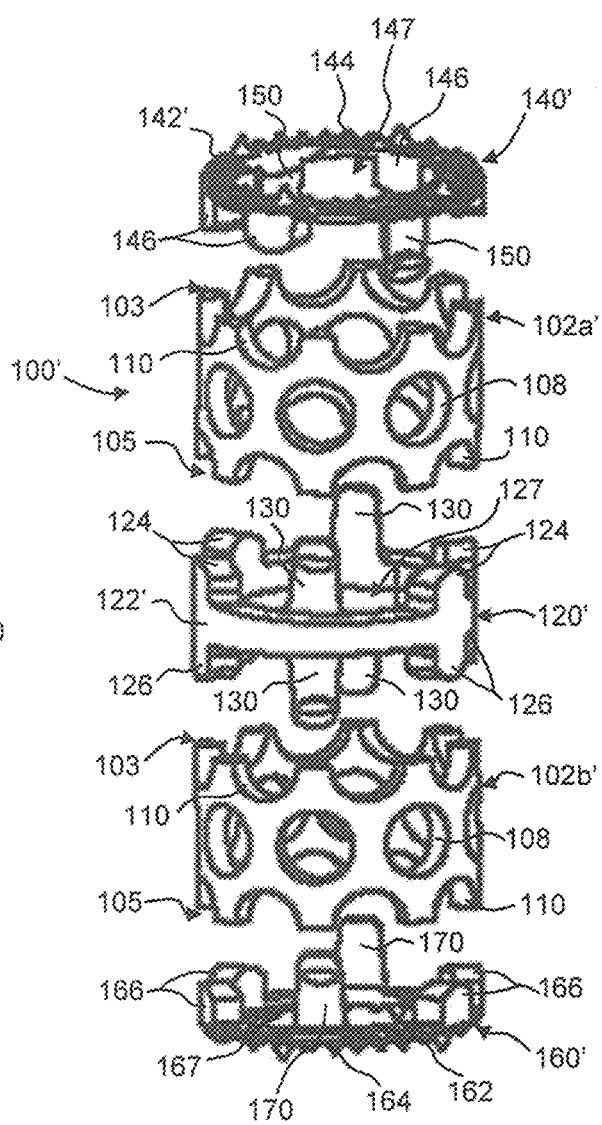
Fig. 6
Fig. 7

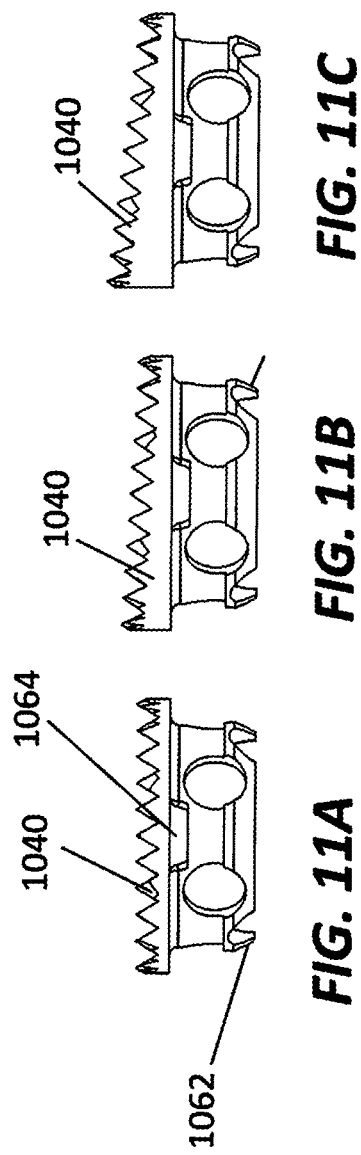

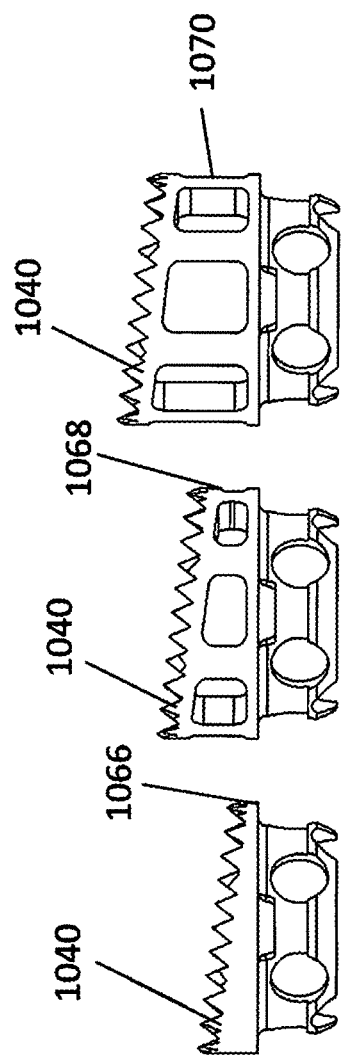

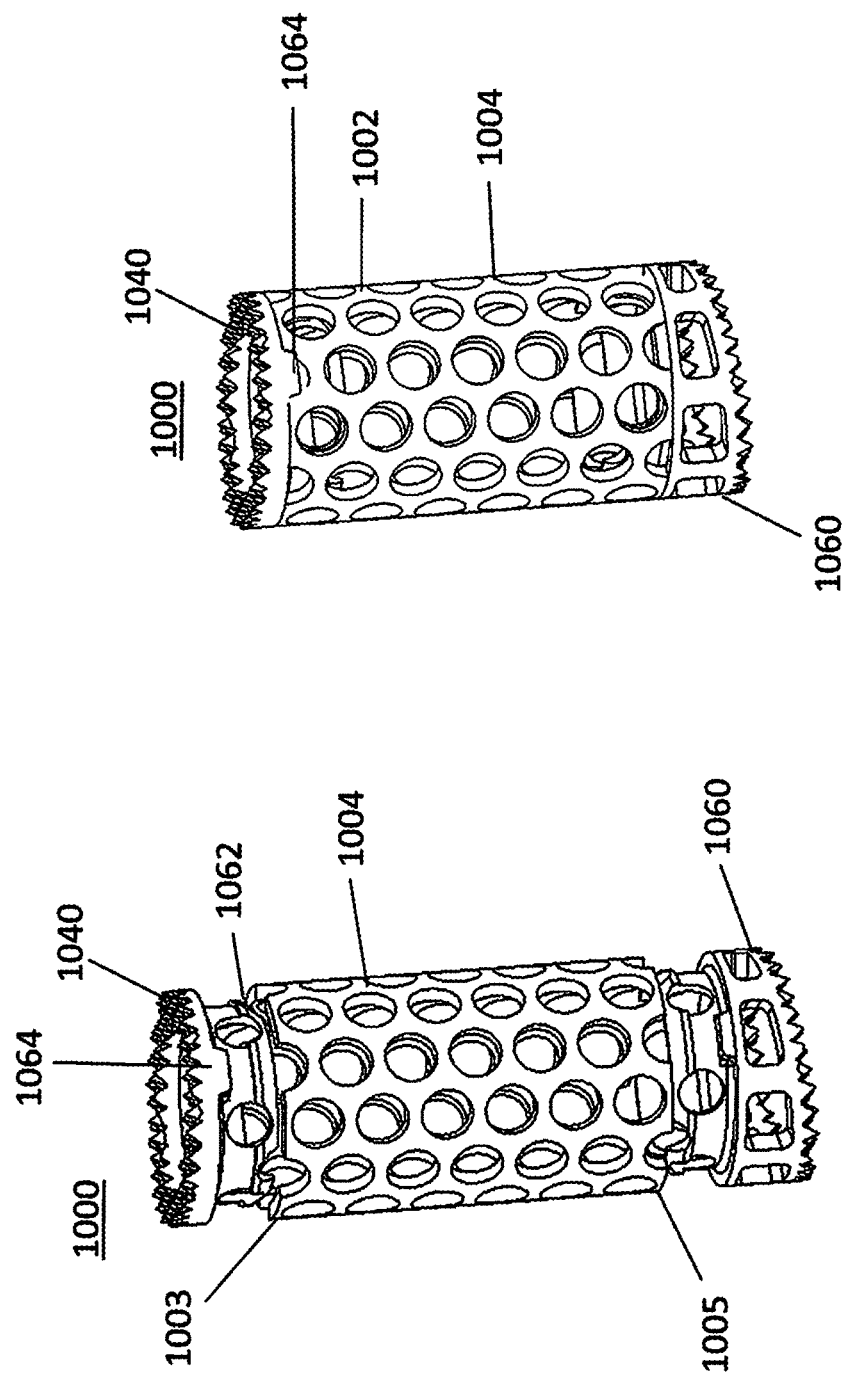

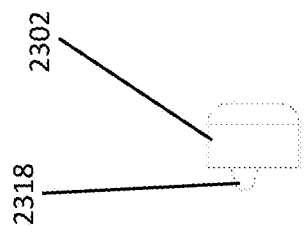
FIG. 25D
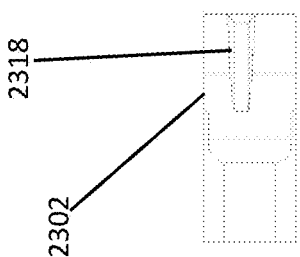
FIG. 25C
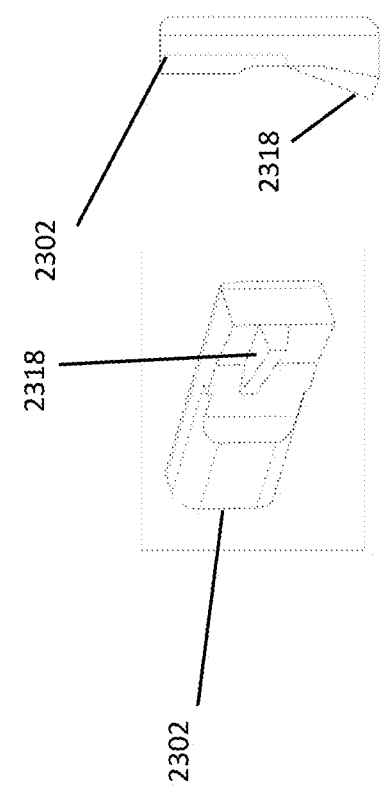
FIG. 25B
FIG. 25A

SYSTEMS AND METHODS FOR EXPANDABLE CORPECTOMY SPACER IMPLANTATION

CROSS-REFERENCE TO RELATED APPLICATION

This application is a continuation-in-part of U.S. patent application Ser. No. 16/371,419 (published as U.S. Pat. Pub. 2019-0224023), which is a continuation of U.S. patent application Ser. No. 15/836,362, filed on Dec. 8, 2017 (now U.S. Pat. No. 10,278,834), which is a continuation-in-part application of U.S. patent application Ser. No. 15/264,974 filed on Sep. 14, 2016 (now U.S. Pat. No. 10,278,833), the contents of all of which are incorporated by reference herein in their entirety for all purposes.

FIELD

The present disclosure relates to systems and devices for supporting the spine after removal of at least a part of a vertebra. More particularly, the disclosure relates to vertebral body replacement implant assemblies and attachment assemblies.

BACKGROUND

Diseases and injury to bone structures, such as the vertebral column, and conditions requiring surgical intervention are relatively common. A variety of conventional implant or graft devices are presently available for use in specific areas. The devices vary in size, shape, materials used, and insertion techniques. For example, in the vertebral column, grafts may provide restoration, decompression, or stabilization of the spine. Typically, these devices include a member that is inserted in the vertebral column to replace an injured portion. An example of such a procedure is a corpectomy, which involves the replacement of all or a portion of the vertebral body with an implant or graft. One exemplary graft is a mesh corpectomy cage which is secured to the adjacent vertebrae via end plates to maintain the position of the implant in situ.

While these conventional devices may generally provide adequate results, they have several disadvantages. For example, often with a corpectomy that involves more than one level, the center segment of the corpectomy cage will settle into a position very close to the patient's dura and spinal cord due to the natural lordosis/kyphosis of the patient. Such proximity to the dura and spinal cord may cause pain, discomfort or further damage to the vertebral column.

Additionally, the endplates are typically secured to the cage with screws. The screws are often cumbersome to install and also make it more difficult to safely remove and replace any component of the construct. Furthermore, there is an inherent risk that the screws may be dropped during a procedure.

With respect to expandable vertebral body replacement (VBR) implants and cages, current expandable VBR cages have limited space for packing bone graft materials and are limited in allowing for bone graft material delivery into the implant after expansion. For example, an expansion range of the shortest expandable cage (15 mm) may only allow for 3-4 mm of expansion.

What is needed is an expandable mesh corpectomy spacer (which may also be used as an interbody spacer) that allows for bone graft material delivery after expansion and allows for up greater expansion for an implant with a starting height of 15 mm, for example.

SUMMARY

According to one embodiment, an implant assembly for engagement between a first vertebral body and a second vertebral body includes an inner core extending between a first end and a second end, a first outer core disposed on the first end, and a second outer core disposed on the second end. The inner core may be actuated in a first direction to move the first outer core and second outer core to an expanded configuration and the inner core may be actuated in a second direction to move the first outer core and the second outer core to a collapsed configuration.

According to another embodiment, an implant assembly for engagement between a first vertebral body and a second vertebral body includes an inner core extending between a first end and a second end, a first outer core disposed on the first end, a second outer core disposed on the second end, a first endplate configured to removably attach to the first outer core, and a second endplate configured to removably attach to the second outer core. The inner core may be actuated in a first direction to move the first outer core and second outer core to an expanded configuration and the inner core may be actuated in a second direction to move the first outer core and the second outer core to a collapsed configuration.

BRIEF DESCRIPTION OF THE DRAWINGS

The accompanying drawings, which are incorporated herein and constitute part of this specification, illustrate the presently preferred embodiments of the disclosure, and, together with the general description given above and the detailed description given below, serve to explain the features of the disclosure. In the drawings:

FIG. 6 is an exploded perspective view of the implant assembly of FIG. 1.

FIG. 7 is an exploded perspective view of another exemplary implant assembly.

FIGS. 11A-11C are perspective views of exemplary endcaps.

FIGS. 12A-12C are perspective views of exemplary endcaps.

FIG. 14A is perspective view of an exemplary implant assembly prior to installation of exemplary endcaps.

FIG. 14B is a perspective view of an exemplary implant assembly.

FIGS. 25A-D are perspective views of a locking mechanism for an expandable vertebral body replacement implant.

DETAILED DESCRIPTION

Figure 1:
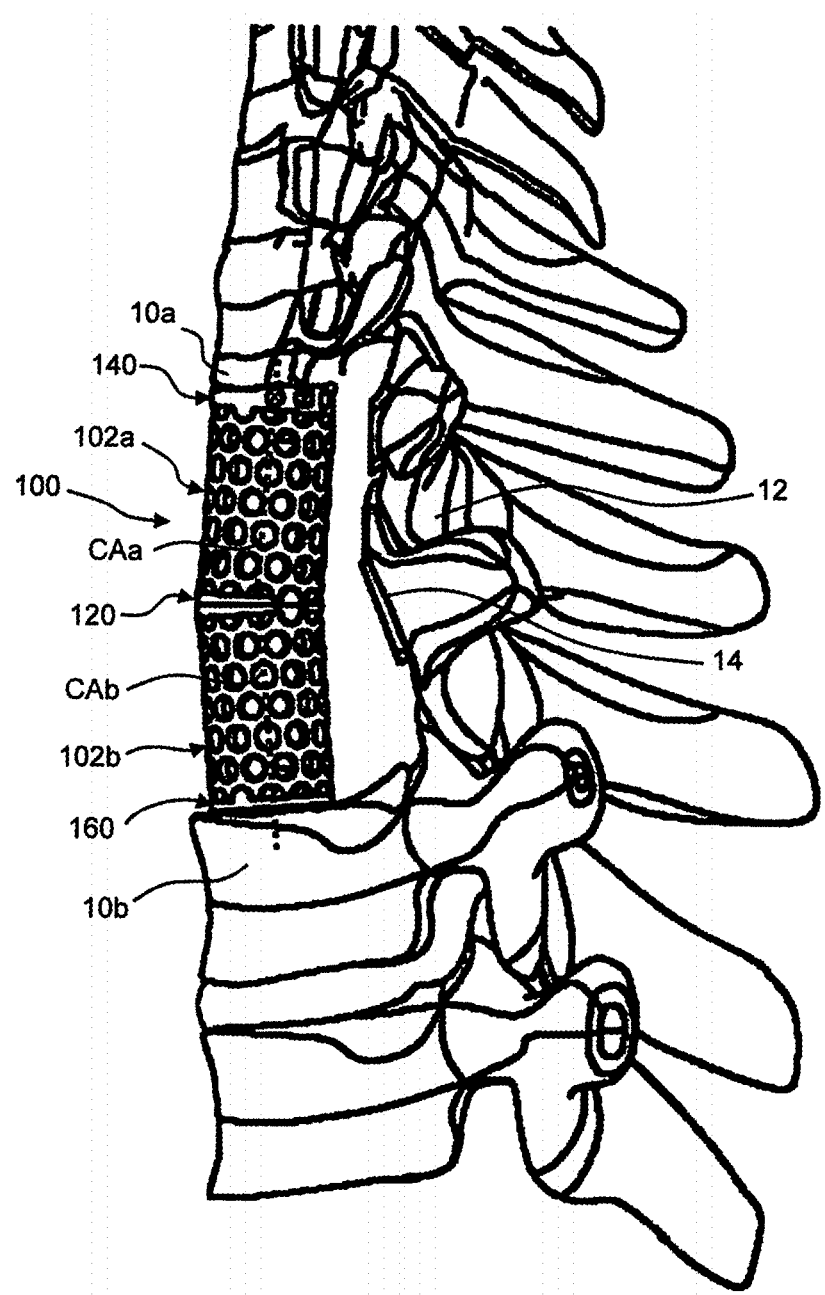
FIG. 1 is a side elevation view of an implant assembly according to an exemplary embodiment attached between vertebrae.

In the drawings, like numerals indicate like elements throughout, with alphabetical or prime identifiers indicating a particular one of the more generally identified element. Certain terminology is used herein for convenience only and is not to be taken as a limitation on the present invention. The following describes preferred embodiments of the present disclosure. However, it should be understood, based on this disclosure, that the invention is not limited by the preferred embodiments described herein.

Referring to FIG. 1, an exemplary implant assembly 100 in accordance with an embodiment of the disclosure is illustrated positioned between a pair of vertebrae 10a, 10b. The implant assembly 100 generally includes two or more mesh cages 102a, 102b, at least one intermediate plate 120 and a pair of endplates 140, 160. The intermediate plate 120 is secured between the cages 102a, 102b and has an angled configuration such that the central axis CAa of the cage 102a is angled at an acute angle α (see FIG. 9) relative to the central axis Cab of the cage 102b. The endplate 140 is secured to the end of cage 102a and secures the cage 102a to the adjacent vertebrae 10a. The endplate 160 is secured to the end of cage 102b and secures the cage 102b to the adjacent vertebrae 10b. The lordotic angle α created by the intermediate plate 120 helps to align the ends of the cages 102a, 102b with the vertebral endplates 10a, 10b which will help in minimizing subsidence. The lordotic angle α also positions the cages 102a, 102b away from the dura 14 and spinal cord 12 of the patient.

Figure 2:
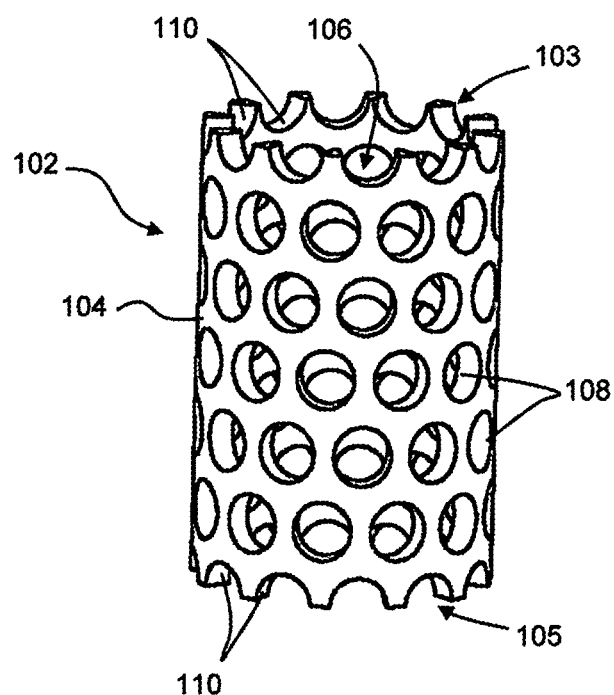
FIG. 2 is a perspective view of an exemplary cage member of the implant assembly of FIG. 1.
Figure 3:
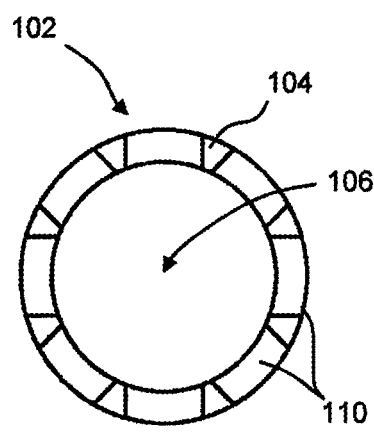
FIG. 3 is a top plan view of the cage member of FIG. 2.
Figure 4:
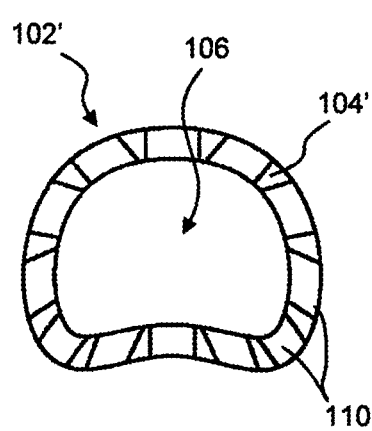
FIG. 4 is a top plan view of an alternative cage member.
Figure 5:
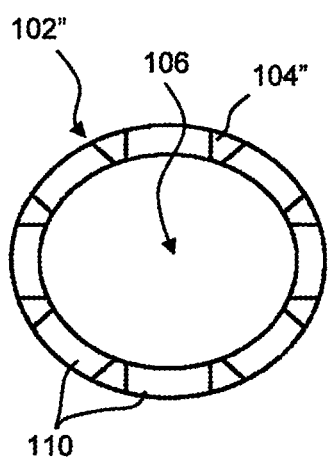
FIG. 5 is a top plan view of yet another alternative cage member.

Referring to FIGS. 2-5, exemplary embodiments of the cage 102 will be described. Each cage 102 generally has a hollow tubular body 104 extending between ends 103, 105 with a passage 106 therethrough. The tubular body 104 may be manufactured from various materials, for example, but not limited to, titanium or other metals, carbon fibers, ceramics, polymers or biocomposites. As illustrated in the embodiment of FIGS. 2 and 3, the exemplary cage 102 has a circular cross-section, however, the cage 102 may have various configurations. As two non-limiting examples, the cage 102' illustrated in FIG. 4 has a kidney shaped cross-section and the cage 102" illustrated in FIG. 5 has an oval cross-section. The mesh cages 102 may be supplied at various convenient lengths or can be cut to size. It is understood that the cages 102a, 102b of the implant assembly 100 may have the same or different lengths.

The tubular body 104 defines a series of radial openings 108 which open into the through passage 106. The radial openings 108 facilitate bone ingrowth and provide connection points for clips on the intermediate plate 120 and the endplates 140, 160, as will be described in more detail hereinafter. The openings 108 are preferably evenly spaced about the tubular body 104 to create a mesh thickness that offers compressive and torsional strength while allowing the cage to be easily cut to length. While the openings 108 are illustrated with a circular configuration, they openings 108 may have other shapes, for example, square or octagon.

Each end 103, 105 of the cage 102 includes a series of end openings 110 which open into the through passage 106 and are also open to the respective end surface of the tubular body 104. The end openings 110 are configured to receive tabs extending from the intermediate plate 120 and the endplates 140, 160 to provide rotational stability. While the end openings 110 are illustrated with a semi-circular configuration, they openings 108 may have other shapes, for example, square or octagon, and may have a depth that is more or less than one-half the width.

Exemplary intermediate plates 120, 120' and endplates 140, 140', 160, 160' will be described with reference to FIGS. 6-9. The differences between the components of the implant assembly 100 of FIG. 6 and the implant assembly 100' of FIGS. 7-9 will be identified, otherwise the components are substantially the same. With respect to the cages, the cages 102a' and 102b' are shorter than the cages 102a and 102b and have an oval configuration instead of the round configuration of the cages 102a and 102b.

Turning to the intermediate plates 120, 120', each plate 120, 120' has a ring shaped body 122, 122' with a passage 127 therethrough. The body 122 has a circular configuration to match that of the cages 102a, 102b while the body 122' has an oval configuration to match that of the cages 102a', 102b'. Each body 122, 122' extends between opposed contact surfaces 121, 123. The contact surfaces 121, 123 are at an angle θ relative to one another. This angle θ between the contact surfaces 121, 123 creates the lordotic angle α between the central axes CAa and Cab of the cages. In the event that more than two cages are utilized, intermediate plates 120 can be positioned between respective cages 102, each with the same or different angles θ.

On each body 122, 122', a plurality of tabs 124 extend from the contact surface 121 and a plurality of tabs 126 extend from the contact surface 123. The tabs 124, 126 have shapes which complement the shape of the end openings 110 such that the tabs 124, 126 are received in and engage the end openings 110 of the respective cages 102. Engagement between the tabs 124, 126 and the end openings 110 provides rotational stability between the intermediate plates 120, 120' and the cages 102. As seen in comparing the intermediate plate 120 with the intermediate plate 120', the number and location of tabs 124, 126 may be varied.

Additionally, the tabs 124, 126 may be eliminated provided the spring clips 130, described below, provide sufficient rotational stability.

A plurality of spring clips 130 extend from each contact surface 121, 123. As seen in comparing the intermediate plate 120 with the intermediate plate 120', the number and location of spring clips 130 may be varied. Each spring clip 130 includes a body 132 extending from the respective surface 121, 123 and defining a retaining ledge 134 spaced from the respective surface 121, 123. The bodies 132 may have different lengths to account for the angle between the contact surfaces 121, 123 such that each of the retaining ledges 134 on respective side of the intermediate plate 120, 120' are co-planar. With the retaining ledges 134 co-planar, the retaining ledges 134 will engage a common row of openings 108 in a respective cage 102 (see FIG. 9). Each spring clip body 132 is elastic such that it bends inward as spring clips 130 pass into the cage through passage 106, but then springs outward as the retaining ledge 134 aligns with a respective opening 108. The bodies 132 may have a tapered end surface to promote the inward bending of the spring clips 130 as they are inserted. The retaining ledges 134 thereby engage the openings 108 and axially secure the intermediate plate 120, 120' to the cages 102. If it is desired to remove the intermediate plate 120, 120' from the cages 102, the retaining ledges 134 are biased inward until they clear the openings 108 and the intermediate plate 120, 120' is easily disconnected.

Turning to the endplates 140, 140', each plate 140, 140' has a ring shaped body 142, 142' with a passage 147 therethrough. The body 142 has a circular configuration to match that of the cage 102a while the body 142' has an oval configuration to match that of the cage 102a'. Each body 142, 142' extends between opposed contact surfaces 141, 143, with the contact surface 141 being a bone contact surface and the contact surface 143 being a cage contact surface. The contact surfaces 141, 143 of the endplate 140 are at an angle β relative to one another while the contact surfaces 141, 143 of the endplate 140' are parallel to one another. The endplates 140, 140' can have an angled or parallel configuration. This angle θ, or lack of angle, between the contact surfaces 141, 143 allows the surgeon to make an implant assembly 100, 100' unique to the patient's anatomy.

On each body 142, 142', a plurality of projections 144 or the like extend from the contact surface 141 and are configured to engage the vertebrae contact surface. Various surface configurations may be utilized to achieve a desired securement with the vertebrae contact surface. Additionally, the body 142 may include radial openings 145 which promote bone growth into the endplate 140.

Similar to the intermediate plates, a plurality of tabs 146 extend from the contact surface 143. The tabs 146 have shapes which complement the shape of the end openings 110 such that the tabs 146 are received in and engage the end openings 110 of the respective cages 102. Engagement between the tabs 146 and the end openings 110 provides rotational stability between the endplates 140, 140' and the cages 102. As seen in comparing the endplate 140 with the endplate 140', the number and location of tabs 146 may be varied. Additionally, the tabs 146 may be eliminated provided the spring clips 150, described below, provide sufficient rotational stability.

A plurality of spring clips 150 extend from the contact surface 143. As seen in comparing the endplate 140 with the endplate 140', the number and location of spring clips 150 may be varied. Each spring clip 150 includes a body 152 extending from the surface 143 and defining a retaining ledge 154 spaced from the surface 143. With the endplate 140, the bodies 152 may have different lengths to account for the angle between the contact surfaces 141, 143 such that each of the retaining ledges 154 of the intermediate plate 140 are co-planar. With the endplate 140', the bodies 152 will have a common length such that the retaining ledges 154 are co-planar. With the retaining ledges 154 co-planar, the retaining ledges 154 will engage a common row of openings 108 in a respective cage 102 (see FIG. 9). Each spring clip body 152 is elastic such that it bends inward as spring clips 150 pass into the cage through passage 106, but then springs outward as the retaining ledge 154 aligns with a respective opening 108. The bodies 152 may have a tapered end surface to promote the inward bending of the spring clips 150 as they are inserted. The retaining ledges 154 thereby engage the openings 108 and axially secure the endplate 140, 140' to the cage 102. If it is desired to remove the endplate 140, 140' from the cage 102, the retaining ledges 154 are biased inward until they clear the openings 108 and the endplate 140, 140' is easily disconnected.

Turning to the endplates 160, 160', each plate 160, 160' has a ring shaped body 162, 162' with a passage 167 therethrough. The body 162 has a circular configuration to match that of the cage 102a while the body 162' has an oval configuration to match that of the cage 102a'. Each body 162, 162' extends between opposed contact surfaces 161, 163, with the contact surface 161 being a bone contact surface and the contact surface 163 being a cage contact surface. In the illustrated embodiments, the contact surfaces 161, 163 of each of the endplates 160, 160' are parallel to one another, however, it is understood that the surfaces 161, 163 may be angled relative to one another to allow the surgeon to make an implant assembly 100, 100' unique to the patient's anatomy.

On each body 162, 162', a plurality of projections 164 or the like extend from the contact surface 161 and are configured to engage the vertebrae contact surface. Various surface configurations may be utilized to achieve a desired securement with the vertebrae contact surface.

Similar to the intermediate plates, a plurality of tabs 166 extend from the contact surface 163. The tabs 166 have shapes which complement the shape of the end openings 110 such that the tabs 166 are received in and engage the end openings 110 of the respective cages 102. Engagement between the tabs 166 and the end openings 110 provides rotational stability between the endplates 160, 160' and the cages 102. As seen in comparing the endplate 160 with the endplate 160', the number and location of tabs 166 may be varied. Additionally, the tabs 166 may be eliminated provided the spring clips 170, described below, provide sufficient rotational stability.

A plurality of spring clips 170 extend from the contact surface 163. As seen in comparing the endplate 160 with the endplate 160', the number and location of spring clips 170 may be varied. Each spring clip 170 includes a body 172 extending from the surface 163 and defining a retaining ledge 174 spaced from the surface 163. With each of the endplates 160, 160', the bodies 172 will have a common length such that the retaining ledges 174 are co-planar. With the retaining ledges 174 co-planar, the retaining ledges 174 will engage a common row of openings 108 in a respective cage 102 (see FIG. 9). Each spring clip body 172 is elastic such that it bends inward as spring clips 170 pass into the cage through passage 106, but then springs outward as the retaining ledge 174 aligns with a respective opening 108. The bodies 172 may have a tapered end surface to promote the inward bending of the spring clips 170 as they are inserted. The retaining ledges 174 thereby engage the openings 108 and axially secure the endplate 160, 160' to the cage 102. If it is desired to remove the endplate 160, 160' from the cage 102, the retaining ledges 174 are biased inward until they clear the openings 108 and the endplate 160, 160' is easily disconnected.

Figure 8:
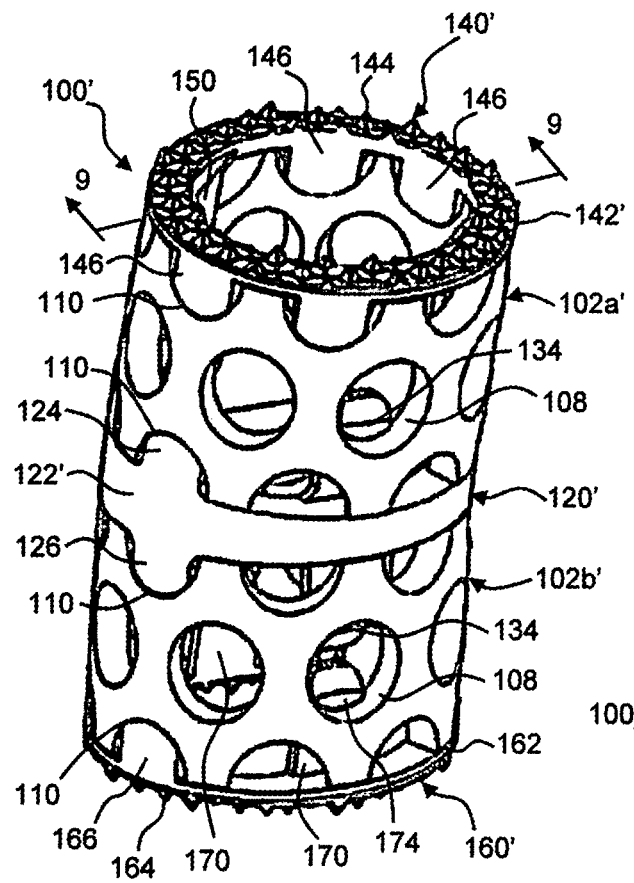
FIG. 8 is a perspective view of the implant assembly of FIG. 7 in an assembled configuration.
Figure 9:
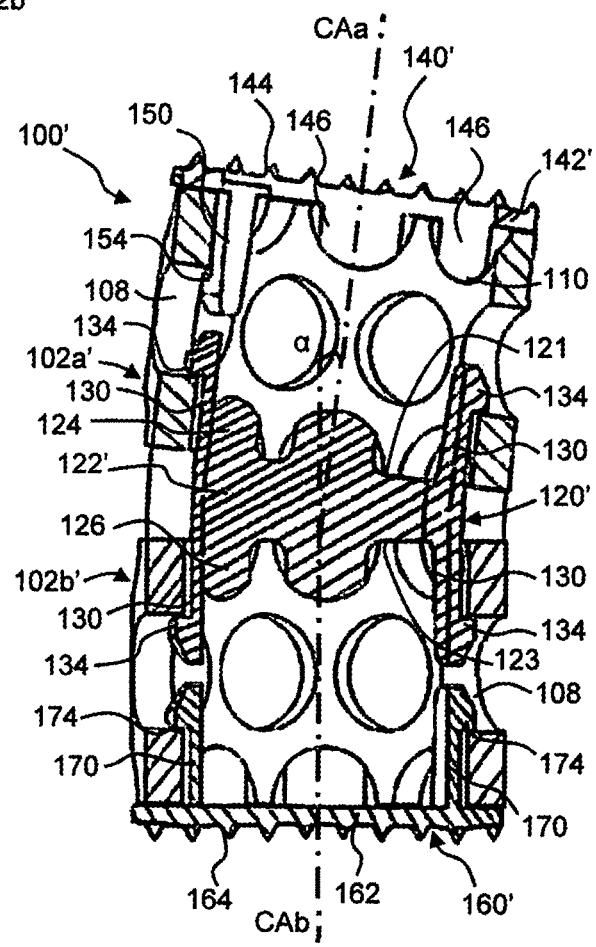
FIG. 9 is a cross-sectional view along the line 9-9 in FIG. 8.
Figure 10:
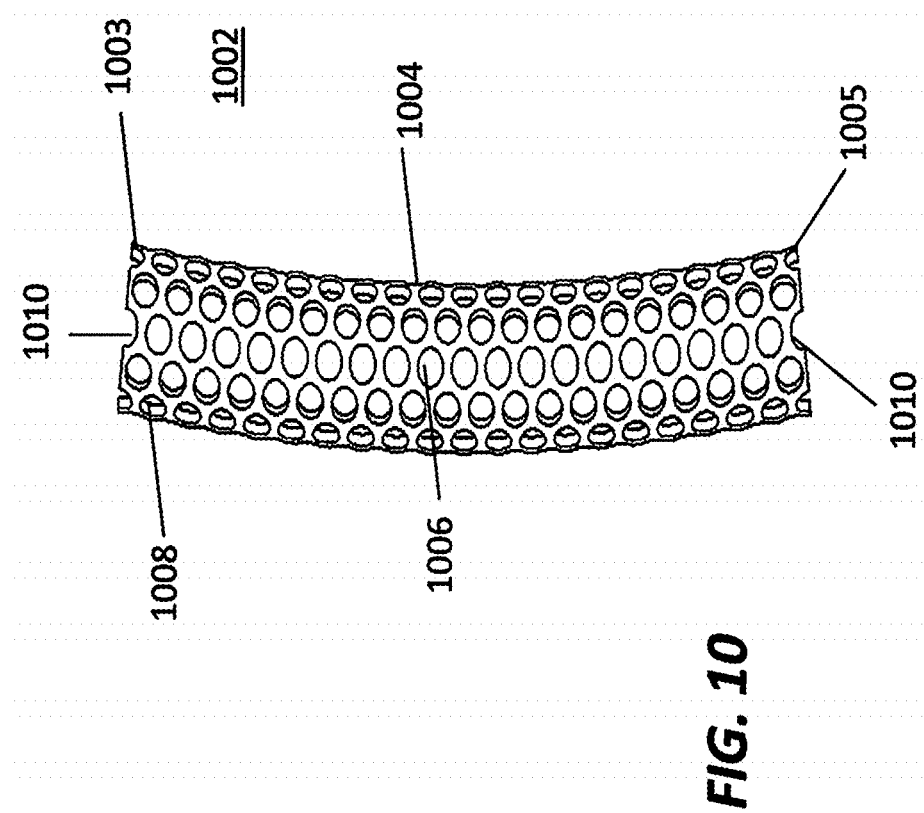
FIG. 10 is a perspective view of an exemplary cage member.

Upon assembly of the implant assemblies 100, 100', as illustrated in FIGS. 1 and 8-9, the integrated clips 130, 150, 170 on the intermediate plate and endplates snap into the corresponding holes 108 in the mesh cages 102 for a secure fit. The quick clip system makes a secure construct while allowing for components to be removed and replaced prior to insertion into the body should the need arise. The intermediate plate 120 offers a safe and secure connection to the mesh cages 102 while providing lordosis/kyphosis at the center of the construct instead of at the end of the cage only. This allows for the body of the implant assembly to be moved away from the dura and spinal cord of the patient.

Figure 15B:
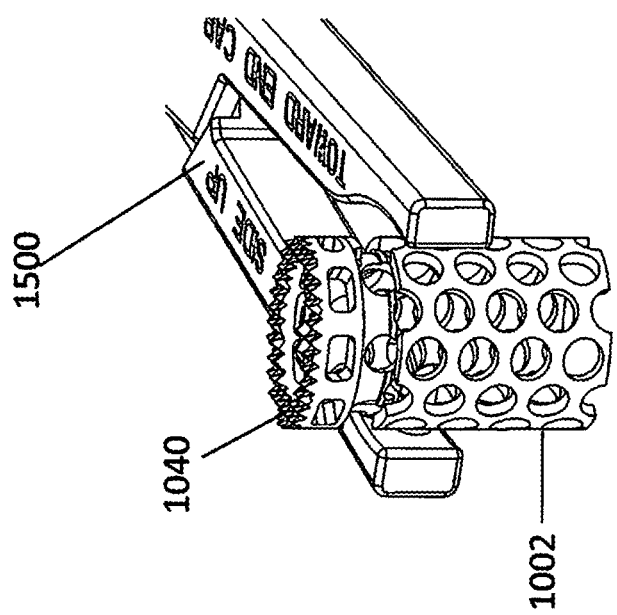
FIGS. 15A-15B are perspective views of an exemplary removal tool.
Figure 15A:
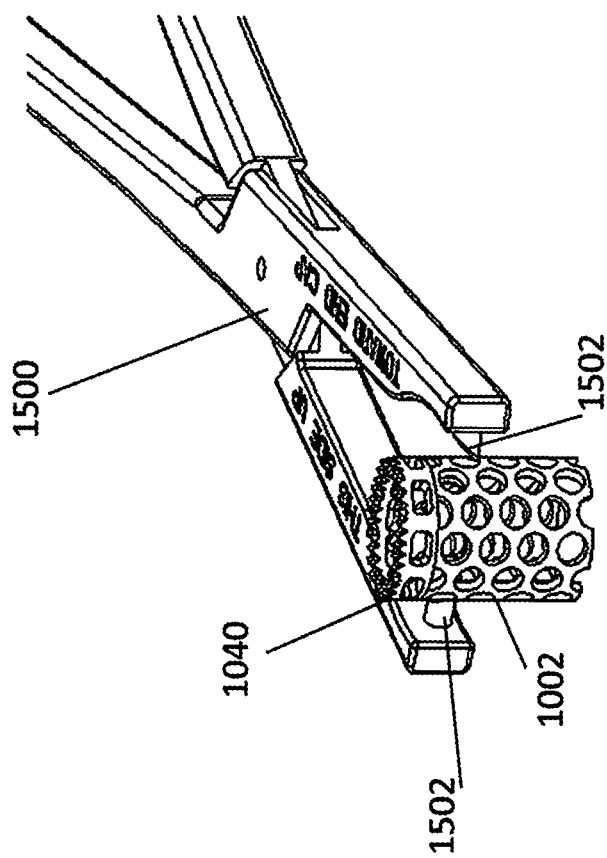

In a further embodiment, FIGS. 10-15B relate to components for an implant assembly 1000 (shown in FIGS. 15A-15B). Implant assembly 1000 is similar in structure to implant assembly 100 but does not contain, at least, the intermediate plates as discussed above. In FIGS. 10-15B, a cage 1002 generally has a hollow tubular body 1004 extending between ends 1003, 1005 with a passage 1006 therethrough. The tubular body 1004 may be manufactured from various materials, for example, but not limited to, titanium or other metals, carbon fibers, ceramics, polymers or biocomposites. Similar to the cage 102, cage 1002 may have a circular cross-section, a kidney shaped cross-section, or an oval cross-section as shown in FIGS. 2-5. The cage 1002 may be supplied at various convenient lengths or can be cut to size. Cage 1002 is illustrated as being curved so that a center section of cage 1002 may be positioned away from dura and spinal cord as previously discussed with respect to cage 102 shown in FIG. 1.

The tubular body 1004 may define a series of radial openings 1008 which open into the passage 1006. The radial openings 1008 may facilitate bone ingrowth and provide connection points for endplates 1040, 1060, as will be described in more detail hereinafter. The openings 1008 are preferably evenly spaced about the tubular body 1004 to create a mesh thickness that offers compressive and torsional strength while allowing the cage to be easily cut to length. While the openings 1008 are illustrated with a circular configuration, the openings 1080 may have other shapes, for example, square or octagon.

Each end 1003, 1005 of the cage 1002 includes at least one end opening 1010 which opens into the through passage 1006 and is also open to the respective end surface of the tubular body 1004. The end openings 1010 are configured to receive a tab 1064 extending from the endplates 1040, 1060 to provide rotational stability. While the end openings 1010 are illustrated with a semi-circular configuration, the openings 1010 may have other shapes, for example, square or octagon, and may have a depth that is more or less than one-half the width. Endplates 1040 and 1060 may be configured to have a tapered end 1062 that allows a tapered lead in point for the endplate 1040, 1060 when inserted into cage 1002. Endplates 1040 and 1060 are configured to press-fit or snap-fit into an end of cage 1002. A final fit may be achieved when an underside of an endplate is flush with an end of cage 1002 and tab 1064, which may be an anti-torsion tab, is seated in a partial hole, such as opening 1010.

The end caps may be angled with optional heights that a surgeon may use to make an implant assembly (e.g., implant assembly 1000) that is tailored to a specific patient's anatomy. Endcaps 1040 and 1060 may be accurately centered to each other and the cage 1002 by means of radial holes 1008 in cage 1002.

As shown in FIGS. 11A-12C, endcaps 1040 (and endcaps 1060) may have a variety of lordotic options that will allow a surgeon to choose an end cap that will closely match the lordosis of the patient. FIGS. 11A-C illustrate varying angles of endcap 1040. FIGS. 12A-C illustrate varying heights of endcap 1040. Further, each end cap 1040, 1060 may be available in a number of height options. For example, FIG. 12A may correspond to a height 1066 of 1.5 mm, FIG. 12B may correspond to a height 1068 of 3.5 mm, and FIG. 12C may correspond to a height 1068 of 5.5 mm. Varying height options may allow a surgeon to quickly remove and replace an end cap 1040 in the case when an implant assembly 1000 is too short or too long. An end cap removal tool 1500 may be supplied to facilitate the change. For example, as shown in FIGS. 15A-15B, removal tool 1500 may include opposing projections 1502 that are configured in a way to enter one of openings 1008 to engage tapered ends 1064 of the applicable endplate to remove the endplate out of cage 1002.

Figure 13B:
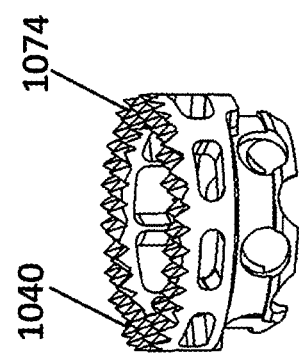
FIG. 13B is a perspective view of an exemplary endcap.
Figure 13A:
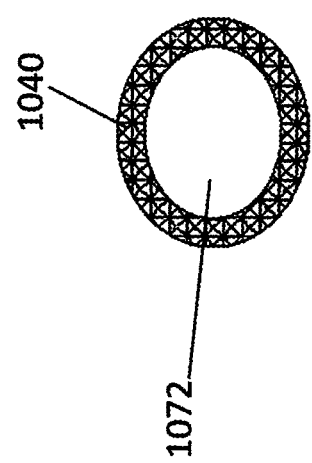
FIG. 13A is a top view of an exemplary endcap.

As shown in FIGS. 13A-13B, an inner geometry 1072 of end cap 1040 may be free of mechanical protrusions, which may allow for a maximum graft window for insertion of bone growth material. A top surface of end cap 1040 may contain teeth 1074 (with or without a laser etched surface) that may aid implant assembly 1000 to grip a vertebral endplate and promote bony ingrowth.

Figure 16:
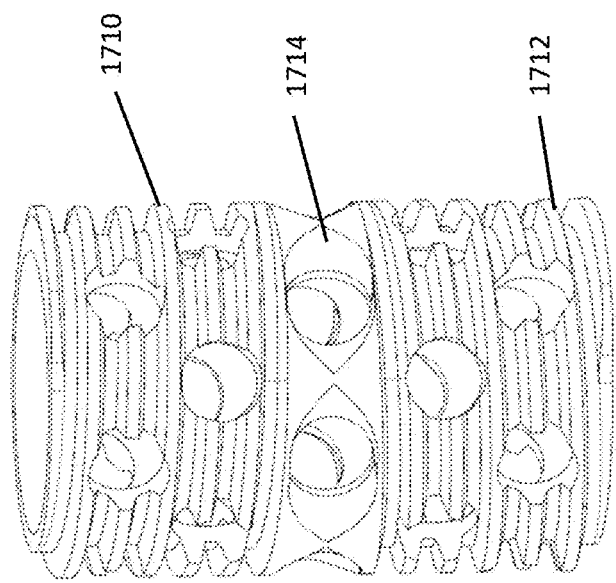
FIG. 16 is a perspective view of an exemplary inner core of an expandable vertebral body replacement implant.
Figure 17B:
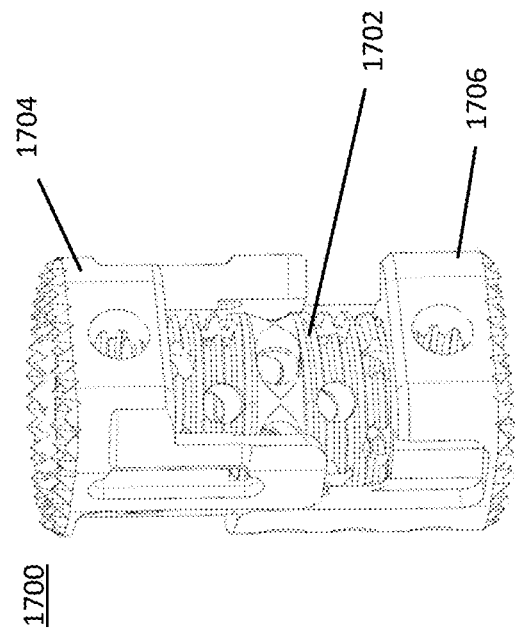
FIGS. 17A and 17B are perspective views of an expandable vertebral body replacement implant.
Figure 17A:
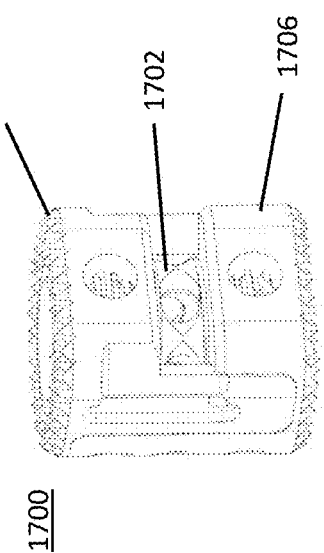
Figure 18:
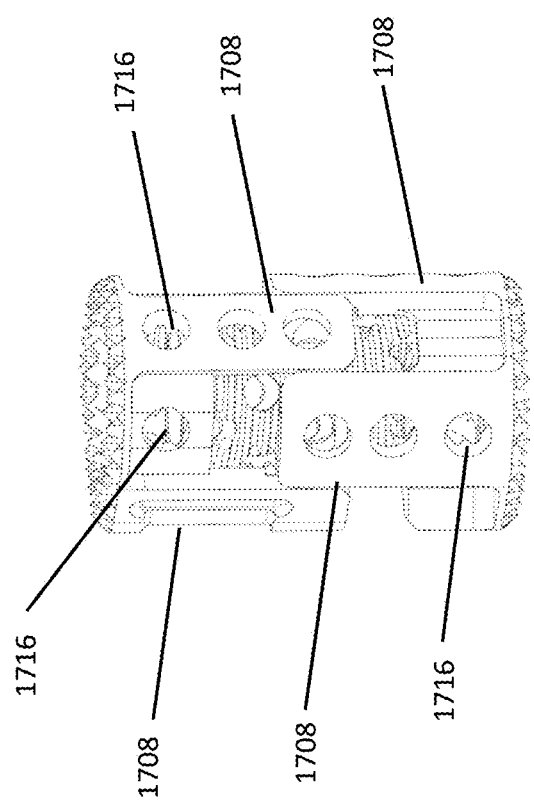
FIG. 18 is a perspective views of an expandable vertebral body replacement implant in an expanded configuration.

Referring now to FIGS. 16-18, an exemplary implant assembly 1700 in accordance with an embodiment of the disclosure is illustrated. Assembly 1700 is an expandable vertebral body replacement (VBR) implant. It may be used for corpectomies or as another type of interbody implant. Assembly 1700 may include three components. One component may be an inner core 1702 with a left-hand thread at one end and a right-hand thread at the opposite end. The other two components may be two outer cores 1704, 1706, one with left-hand internal threads and one with right-hand internal threads. Each outer core 1704, 1706 has mating rails 1708 (or fingers) that prevent torsional spin while allowing expansion, as illustrated in FIG. 18. Assembly 1700 may be locked into final position by a variety of mechanisms, including as described in greater detail with respect to FIGS. 23A-26.

An exemplary inner core 1702 is illustrated in FIG. 16. Inner core 1702 may have a left-handed thread at one end 1710 and a right-handed thread at the opposite end 1712. As inner core 1702 is turned in one direction by an inserter instrument via the set of center holes 1714, the implant 1700 expands as illustrated in FIGS. 17A and 17B. As an example, implant 1700 may allow for up to 8 mm of expansion for an implant with a starting height of 15 mm. Turned in the opposite direction, the implant contracts. The rails 1708 on outer cores 1704, 1706 mate to allow the outer cores 1704, 1706 to expand and prevent spin. Implant 1700 may be configured to be packed with bone graft material after expansion which may aid in fusion of the vertebral bodies through windows 1716.

Referring now to FIGS. 19A-22B, illustrated are exemplary embodiments of removable endplates 1902 for an expandable VBR assembly. By way of background, current VBR cages have endplates that attach to the end of the cage with screws. These screws may be easily dropped and add an extra step to expandable VBR assembly 1700 or 1900.

Figure 19C:
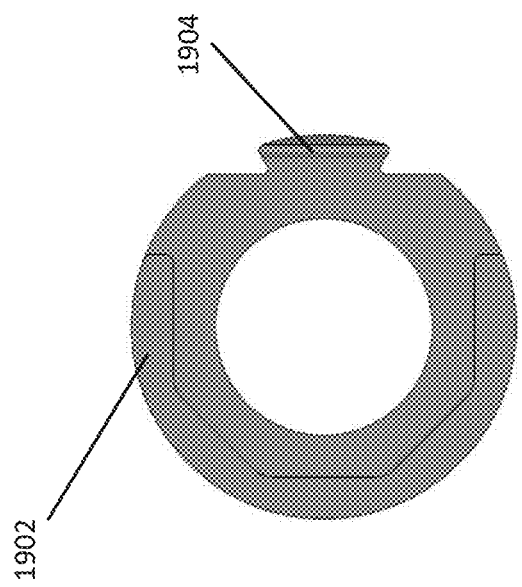
FIG. 19C is a top view of an expandable vertebral body replacement implant with an attached removable end plate.
Figure 19B:
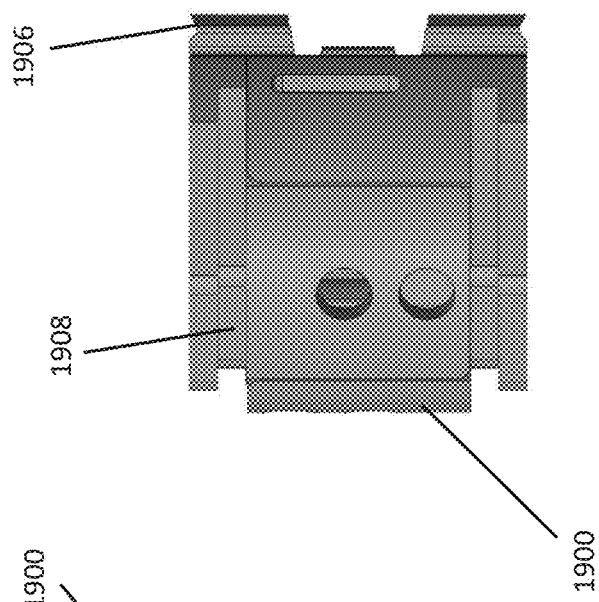
FIG. 19B is a perspective view of an expandable vertebral body replacement implant.
Figure 19A:
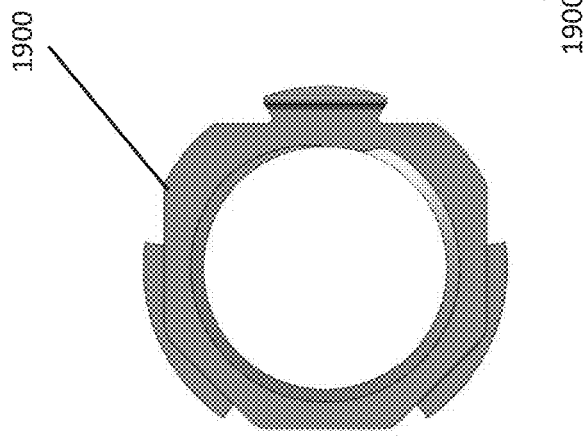
FIG. 19A is a top view of an expandable vertebral body replacement implant.

FIG. 19A illustrates an exemplary expandable VBR assembly 1900 from a top view and FIG. 19B illustrates assembly 1900 in a collapsed configuration from the side. FIG. 19C shows an underside of endplate 1902. Endplate 1902 may be an endplate that slides onto the end of the implant 1900 and configured to snap into place. The may be achieved by using a machined geometric relief 1904 on endplate 1902 and counter-relief 1906 on the implant assembly 1900. Endplate 1902 may slide into place with the use of a standard dado or undercut 1908. Undercut 1908 may be configured to prevent endplate 1902 from lifting off of assembly 1900.

Figure 20B:
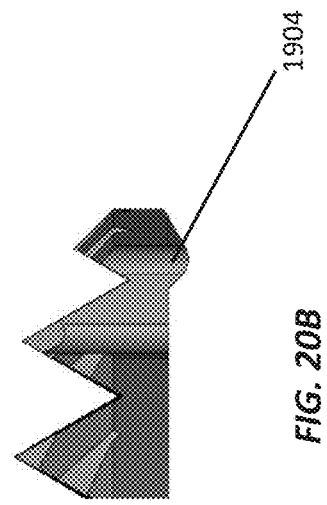
FIGS. 20A-20B are perspective views of an exemplary removable end plate for an expandable vertebral body replacement implant.
Figure 20A:
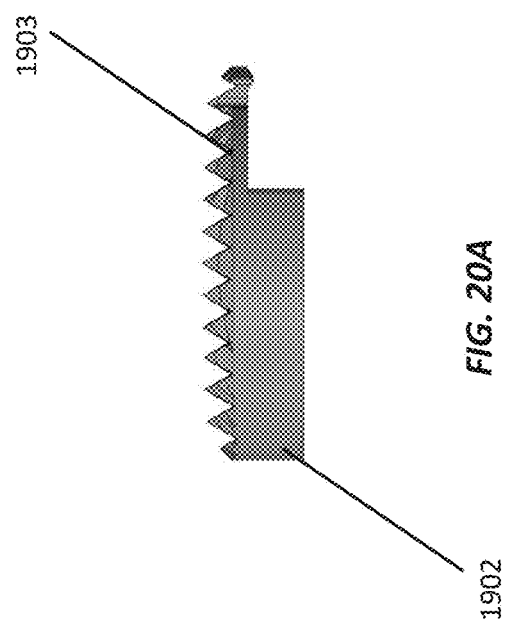
Figure 21:
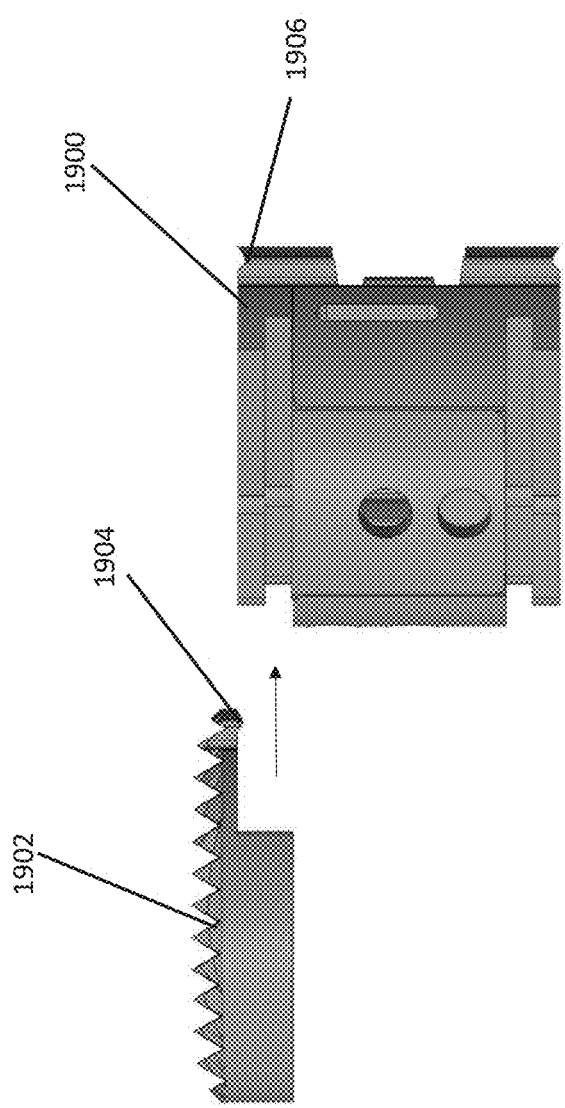
FIG. 21 is a perspective view of a removable endplate detached from an expandable vertebral body replacement implant.
Figures 22A, 22B:
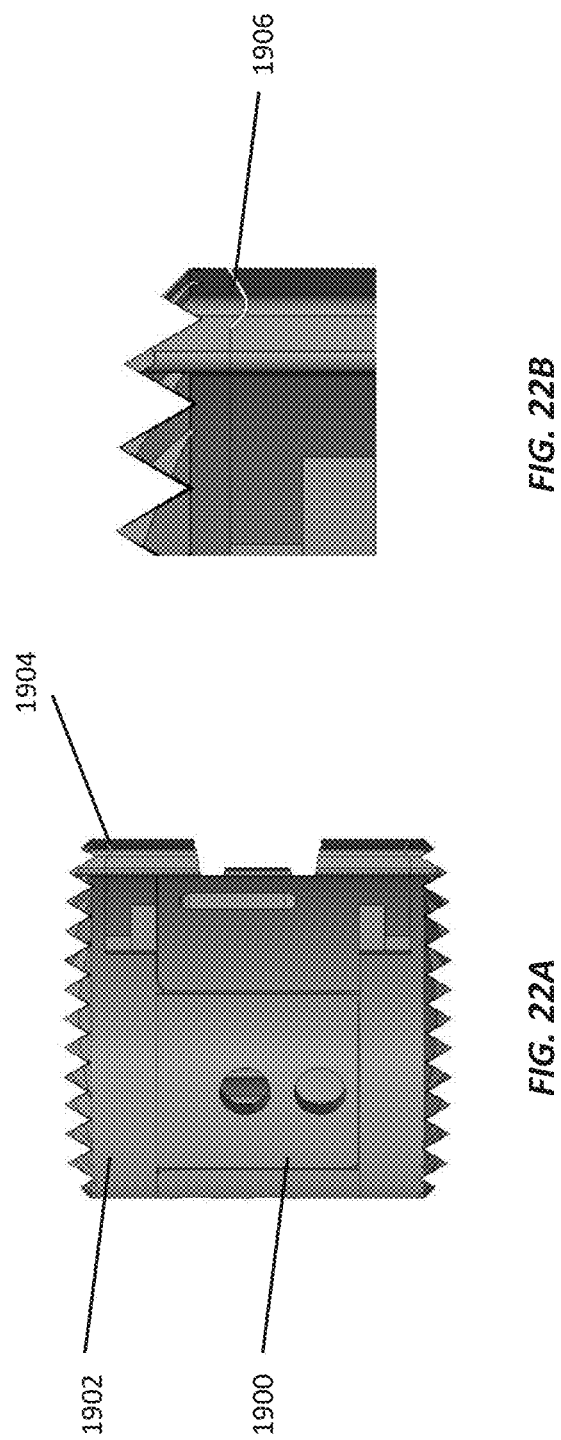
FIGS. 22A-22B are perspective view of a removable endplate attached to an expandable vertebral body replacement implant.

FIG. 20A illustrates a side view of endplate 1902 and FIG. 20B illustrates an expanded view of relief 1904 of endplate 1902. Endplate 1902 may have protrusions 1903 that may engage a vertebral body. As shown in FIG. 21, endplate 1902 is configured to attach to implant assembly 1900 by sliding on either end of assembly 1900. When fully attached, endplate 1902 snaps on the assembly 1900 as illustrated in FIG. 22A. FIG. 22B illustrates an expanded view of relief 1904 and counter-relief 1906 after attachment of endplate 1902. One advantage of the snap is that it eliminates the need for a separate screw to be used to hold endplate 1902 in place on the assembly 1900. It may also eliminates the need of an assembly block or fixture.

Referring now to FIGS. 23A-26B, an exemplary expandable VBR assembly 2300 consistent with the principles of the present disclosure is illustrated. Here, assembly 2300 includes a locking mechanism 2302. By way of background, expandable VBR cages need to be locked so as to prevent them from collapsing or losing height due to the natural vibration and/or movement of the human body into which they are implanted. Current implants available often use a locking screw that needs to be manually locked by the surgeon as a final step of the surgery. Due to the location in the body and approach of a corpectomy and the small size of the implant, the small size of the locking screw head and accessibility to it may prove to be difficult for the surgeon to locate, align and lock.

As shown in FIGS. 23A-26B, assembly 2300 may have locking mechanism 2302, which may be an automatic locking system for a surgical implant that securely locks the implant when the instrument that is used to insert the implant into the body is removed. This may eliminate the need to manually lock the implant as a final surgical step.

Assembly 2300 may have locking mechanism 2302 to automatically lock assembly 2300 in any position to prevent it from moving, winding down or collapsing from weight, external interference, movement or vibration. Locking mechanism may be seated within the interior portion of assembly 2300, with a visible gage to indicate that locking mechanism 2302 is locked or unlocked. The lock functions in conjunction with right-hand and left-hand threads as described earlier. The implant may contain one or two locks depending on size. For purpose of illustration, one lock is shown.

Figure 23A:
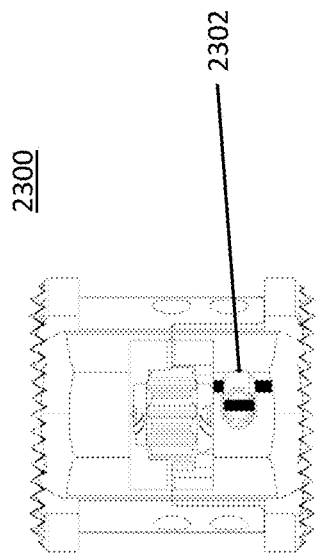
FIGS. 23A-B are perspective views of a an expandable vertebral replacement implant.
Figure 23B:
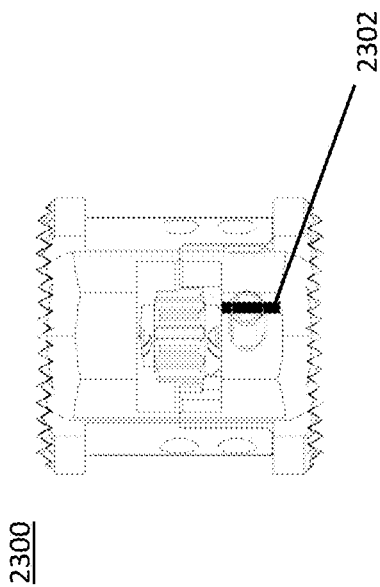

As shown in FIGS. 23A and 23B, when locking mechanism is engaged, an etched or engraved lines will be aligned to visually form a solid line as shown in FIG. 23A. In the unlocked position, the lines will appear separated or perpendicular to one another, as shown in FIG. 23B.

Figure 24:
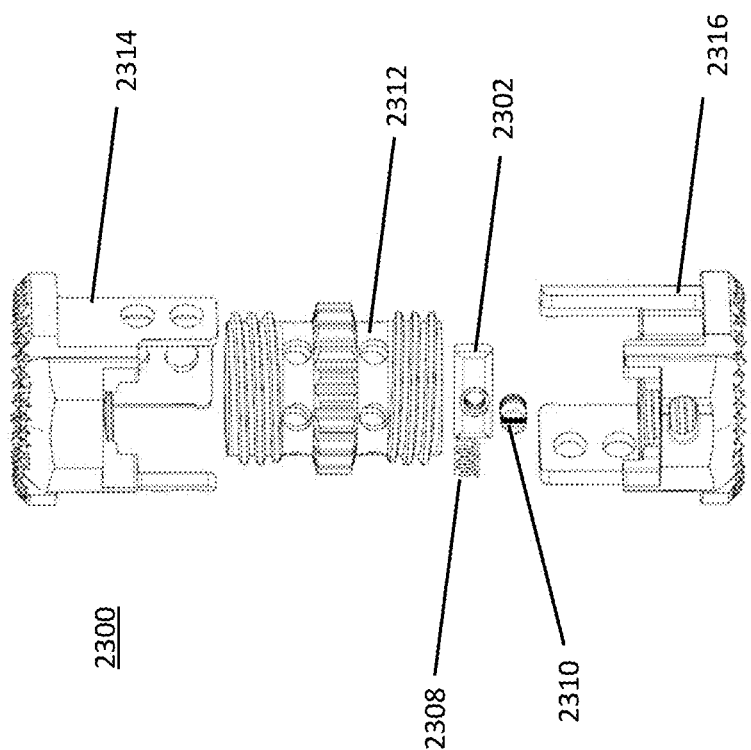
FIG. 24 is an exploded view of an expandable vertebral replacement implant.

An exploded view of assembly 2300 is illustrated in FIG. 24. Assembly 2300 may include locking mechanism 2302, a spring mechanism 2308, a lock indicator 2310, inner core 2312 which may function as a threaded actuator as previously described, an outer core 2314 (right handed (RH) end), and an outer core 2316 (left handed (LH) end).

In practice, locking mechanism 2302 may be positioned inside of a cavity in outer core 2314 (RH end) or outer core 2316 (LH End) of assembly 2300. Spring mechanism 2308 assists by keeping constant tension on locking mechanism 2302 in the "locked" position. Spring mechanism 2308 is illustrated as a coiled compression spring. It may also take the form of a constant tension spring, a leaf spring, or any other form that exerts pressure against the locking mechanism 2302. Locking mechanism 2302 is disengaged into the un-locked position by a portion of the insertion instrument in the form of a wedge, clamp or screw, thereby allowing the implant to be expanded or contract by means of a drive gear. When the insertion instrument is removed from assembly 2300, locking mechanism 2302 is engaged as spring mechanism 2308 pushes locking mechanism 2302 into the locked position.

As illustrated in FIGS. 25A-25D, locking mechanism 2302 may be a tapered block tangent to the major diameter of the inner core 2312, with a centered tooth 2318, or multiple teeth, that are oversized to the minor diameter of inner core 2312. As locking mechanism 2302 is pushed into position, it wedges itself against the inner core 2312 and outer core 2314 (RH end) or outer core 2316 (LH end) to act as a "doorstop," preventing assembly 2300 from further movement.

Figure 26A:
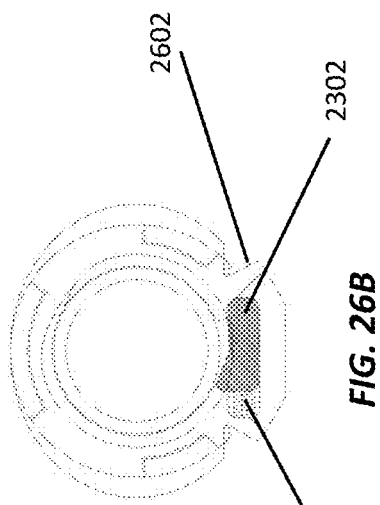
FIGS. 26A-B are top views of expandable vertebral replacement implant.
Figure 26B:
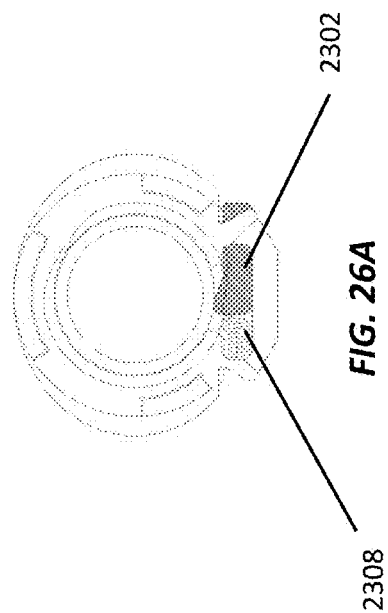

FIG. 26A illustrates assembly 2300 in a locked position and FIG. 26B shows assembly 2300 in an unlocked position. At instrument insertion point 2602, an instrument pushes against locking mechanism 2302 to unlock assembly 2300 to expand or contract assembly 2300. One advantage of this configuration is that the locking of assembly 2300 occurs automatically once the insertion instrument is removed. The lock is not subject to surgical approach, visual alignment or physical access to a separate locking screw that may be difficult for the surgeon to see.

These and other advantages of the present disclosure will be apparent to those skilled in the art from the foregoing specification. Accordingly, it will be recognized by those skilled in the art that changes or modifications may be made to the above-described embodiments without departing from the broad inventive concepts. It should therefore be understood that this disclosure is not limited to the particular embodiments described herein, but is intended to include all changes and modifications that are within the scope and spirit of the disclosure as defined in the claims.

What is claimed is:

1. An implant assembly for engagement between a first vertebral body and a second vertebral body comprising:
    an inner core extending between a first end and a second end;
    a first outer core disposed on the first end; and
    a second outer core disposed on the second end,
    wherein the inner core is configured to be actuated in a first direction to move the first outer core and second outer core to an expanded configuration and wherein the inner core is configured to be actuated in a second direction to move the first outer core and the second outer core to a collapsed configuration;
    wherein the first outer core and the second outer core contain one or more mating rails to prevent rotation of the first outer core and the second outer core during expansion.

2. The implant assembly according to claim 1, wherein the first outer core is configured to engage the first vertebral body and the and the second outer core is configured to engage the second vertebral body.

3. The implant assembly according to claim 1, wherein the inner core includes left handed threading on the first end and right handed threading on the second end.

4. The implant assembly according to claim 1, wherein the inner core contains central holes configured to be engaged by an inserter instrument.

5. The implant assembly according to claim 1, wherein the first outer core and the second outer core contain one or more protrusions configured to engage one of the first vertebral body and the second vertebral body.

6. The implant assembly according to claim 1, wherein the first outer core and the second outer core are configured to receive a removable end plate.

7. The implant assembly according to claim 6, wherein the removable endplate contains a relief to engage a counter relief on one of the first outer core and the second outer core.

8. The implant assembly according to claim 1, further comprising a locking mechanism configured to lock the first outer core and the second outer core relative to the inner core.

9. The implant assembly according to claim 8, wherein the locking mechanism is configured to automatically lock the first outer core and the second outer core relative to the inner core via a spring mechanism.

10. An implant assembly for engagement between a first vertebral body and a second vertebral body comprising: an inner core extending between a first end and a second end;
a first outer core disposed on the first end;
a second outer core disposed on the second end;
a first endplate configured to removably attach to the first outer core;
a second endplate configured to removably attach to the second outer core;
wherein the inner core is configured to be actuated in a first direction to move the first outer core and second outer core to an expanded configuration and wherein the inner core is configured to be actuated in a second direction to move the first outer core and the second outer core to a collapsed configuration;
wherein the first outer core and the second outer core contain one or more mating rails to prevent rotation of the first outer core and the second outer core during expansion.

11. The implant assembly according to claim 10, wherein the first endplate is configured to engage the first vertebral body and the and the second endplate is configured to engage the second vertebral body.

12. The implant assembly according to claim 10, wherein the inner core includes left handed threading on the first end and right handed threading on the second end.

13. The implant assembly according to claim 10, wherein the inner core contains central holes configured to be engaged by an inserter instrument.

14. The implant assembly according to claim 10, wherein the first endplate and the second endplate contain one or more protrusions configured to engage one of the first vertebral body and the second vertebral body.

15. The implant assembly according to claim 10, wherein the first outer core and the second outer core contain undercuts configured to engage one of the first endplate and the second endplate.

16. The implant assembly according to claim 15, wherein the first endplate and the second endplate contains a relief to engage a counter relief on one of the first outer core and the second outer core.

17. The implant assembly according to claim 10, further comprising a locking mechanism configured to lock the first outer core and the second outer core relative to the inner core.

18. The implant assembly according to claim 17, wherein the locking mechanism is configured to automatically lock the first outer core and the second outer core relative to the inner core via a spring mechanism.

* * * * *